Figure 1A:
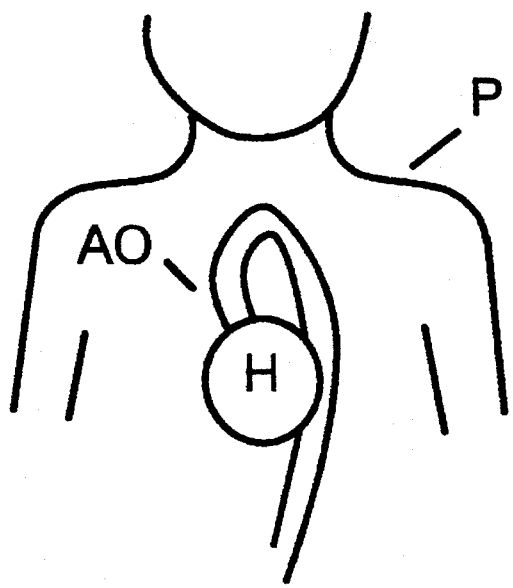

United States Patent [19]

Sepponen

[11] Patent Number: 5,620,003
[45] Date of Patent: Apr. 15, 1997

[54] METHOD AND APPARATUS FOR MEASURING QUANTITIES RELATING TO A PERSONS CARDIAC ACTIVITY

[75] Inventor: Ulla K. Sepponen, Helsinki, Finland

[73] Assignee: Increa Oy, Helsinki, Finland

[21] Appl. No.: 367,349

[22] PCT Filed: Sep. 15, 1993

[86] PCT No.: PCT/FI93/00370

§ 371 Date: Mar. 15, 1995

§ 102(e) Date: Mar. 15, 1995

[87] PCT Pub. No.: WO94/06348

PCT Pub. Date: Mar. 31, 1994

[30] Foreign Application Priority Data

Sep. 15, 1992 [FI] Finland ................... 924117

[51] Int. Cl.⁶ ........................... A61B 5/02
[52] U.S. Cl. ........................... 128/714; 128/774
[58] Field of Search ................... 128/714, 774, 128/782, 779; 364/413.02; 177/245

[56] References Cited

U.S. PATENT DOCUMENTS

| | | |
|---|---|---|
| 2,141,246 | 12/1938 | Jacobus et al. . |
| 2,219,692 | 2/1940 | McDonald ............... 128/714 |
| 3,076,452 | 2/1963 | Rothe ................... 128/714 |
| 3,465,747 | 9/1969 | Rogallo . |
| 4,195,643 | 4/1980 | Pratt, Jr. ................... 128/779 |
| 4,299,233 | 11/1981 | Lemelson . |
| 4,831,527 | 5/1989 | Clark . |
| 4,836,215 | 6/1989 | Lee . |

FOREIGN PATENT DOCUMENTS 1502007  8/1989  U.S.S.R. .

OTHER PUBLICATIONS

Wilbarger, Jr. et al., "Indirect Heart Rate Measuring Device", American Journal of Medical Electronics, Jul.–Sep. 1964, pp. 199 – 200.

Primary Examiner—Angela D. Sykes
Assistant Examiner—Eric F. Winakur
Attorney, Agent, or Firm—Reising, Ethington, Barnard & Perry

[57] ABSTRACT

A method and an apparatus for measuring quantities relating to a person's cardiac activity, such as for example quantities proportional to heart rate, cardiac stroke volume and cardiac output. A person is positioned on a measuring support (S), so that a blood flow pulse caused by a stroke of heart is matched by a change in a person's weight (G). Said change of weight is recorded and the recorded changes of weight are used for deriving information about a person's cardiac activity, such as for example about stroke volume and cardiac output as well as heart rate.

20 Claims, 5 Drawing Sheets

5,620,003

METHOD AND APPARATUS FOR MEASURING QUANTITIES RELATING TO A PERSONS CARDIAC ACTIVITY

The present invention relates to a method and apparatus for measuring quantities relating to the cardiac activity and physical condition of a person, including quantities correlating to the stroke volume and cardiac output which relate to the heart rate and a person's weight and cardiac blood circulation, and for using the measuring results for calculating an index representing the physical condition of a person.

The cardiac pulse rate or heart rate HR, whose unit is pulses per minute as measured in conditions of rest and various stresses, provides e.g. a representation of the physical condition of a person being examined. HR increases not only as a result of mental and physical stress but also various illnesses, for example fever. At rest, HR of a person in a good condition is typically lower than HR of a person in a poor condition.

In the evaluation of the cardiac activity, the measurement of HR only provides highly superficial information. It is also important to know the cardiac stroke volume SV, whose unit is liter, and the cardiac output CO, whose unit is liters per minute. CO is obtained for example by multiplying HR and the average SV with each other.

It is prior known to measure HR by recording electric cardiac activity, a so-called ECG-signal, used for identifying e.g. so-called QRS-complexes. The heart rate is obtained by measuring the time between successive QRS-complexes, whereby the inverse value of said time indicates HR. Devices based on this principle are manufactured for athletes and fitness enthusiasts e.g. by Polar Electro OY, Finland. A drawback in these devices is the necessity of attaching electrodes to the body. Neither does the ECG-signal provide any information about SV or CO.

It is also prior known to measure HR by utilizing variations of electrical impedance and light transmission. Light transmission can be measured e.g. from the earlobe and finger. An HR measuring device for athletes based on light transmission is manufactured e.g. by Casio, Japan. A drawback in this type of methods is that a necessary transducer must be in a good optical contact with a person being examined. With persons in poor condition or in a cold environment, the blood circulation in a finger or an ear may be so weak that the required signal cannot be produced. The light transmission variations caused by peripheral blood circulation do not include information about SV or CO. On the other hand, the CO meters based on electrical impedance variation require that several electrodes be attached to the body.

A person being examined in a ballistiocardiographic apparatus lies on a responsive support and mechanical oscillations resulting from cardiac activity are recorded. In principle, the SV and CO values can be calculated from the amplitude of oscillations. In practice, the results have shown a poor absolute accuracy but measurements at different times on one person are relatively well reproducible. An inconvenience in this method is e.g. the provision of a sufficiently responsive bed for a patient in order to obtain sufficiently accurate measuring results.

It is further known to place a pad underneath a person being examined for producing a piezoelectric signal or some other electric quantity for measuring a person's HR. Such measurements do not provide information about the CO or SV values of a person.

The prior known methods and equipment are neither capable of measuring HR, SV and CO values in a simple manner nor of producing simple indices for monitoring the condition of a person.

The present invention provides a solution for eliminating the deficiencies of prior art and for designing equipment which provide information not only about HR but also about the SV and CO values and the weight of a person. The quantities measured by means of methods and equipment of the invention can be used for producing index numbers for monitoring the progress of a person's condition. In order to achieve this, a method of the invention and apparatus based thereon are characterized by what is set forth in the characterizing sections of the annexed claims.

The most important benefits of the invention include simple operation and inexpensive design and particularly the information provided by methods of the invention and corresponding apparatus about the physical condition of a person.

The invention is illustrated in the accompanying drawings, in which

Figure 1B:
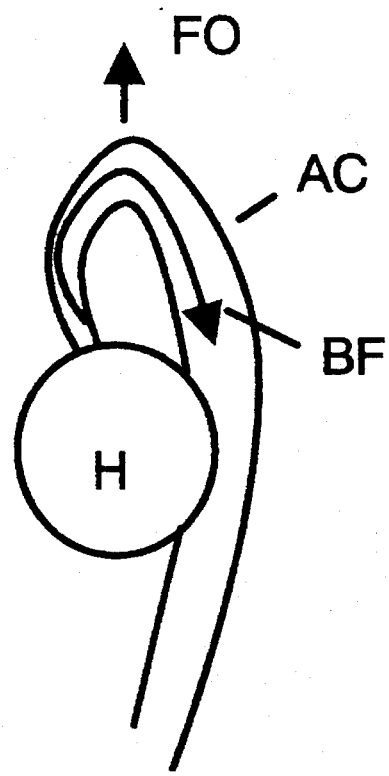
Figure 1C:
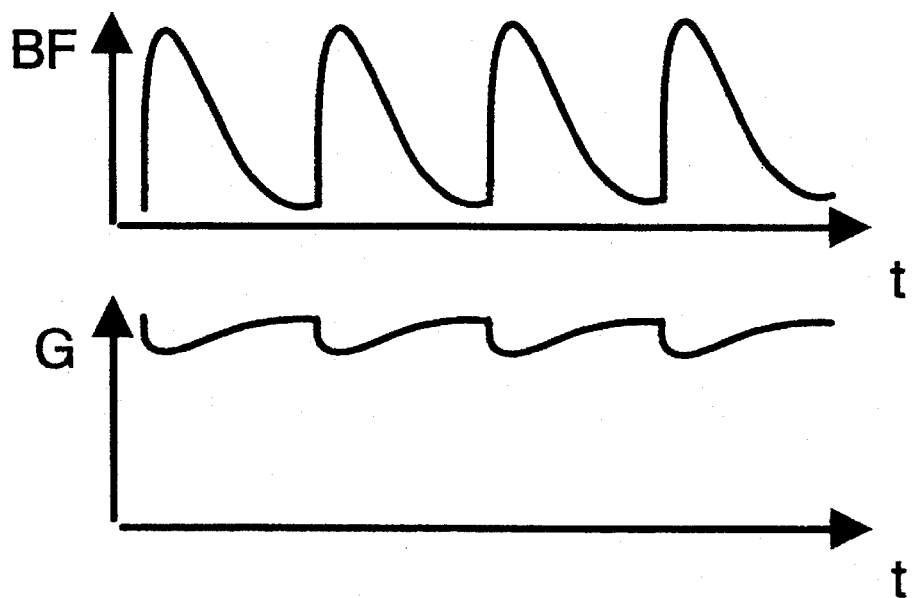
Figure 2:
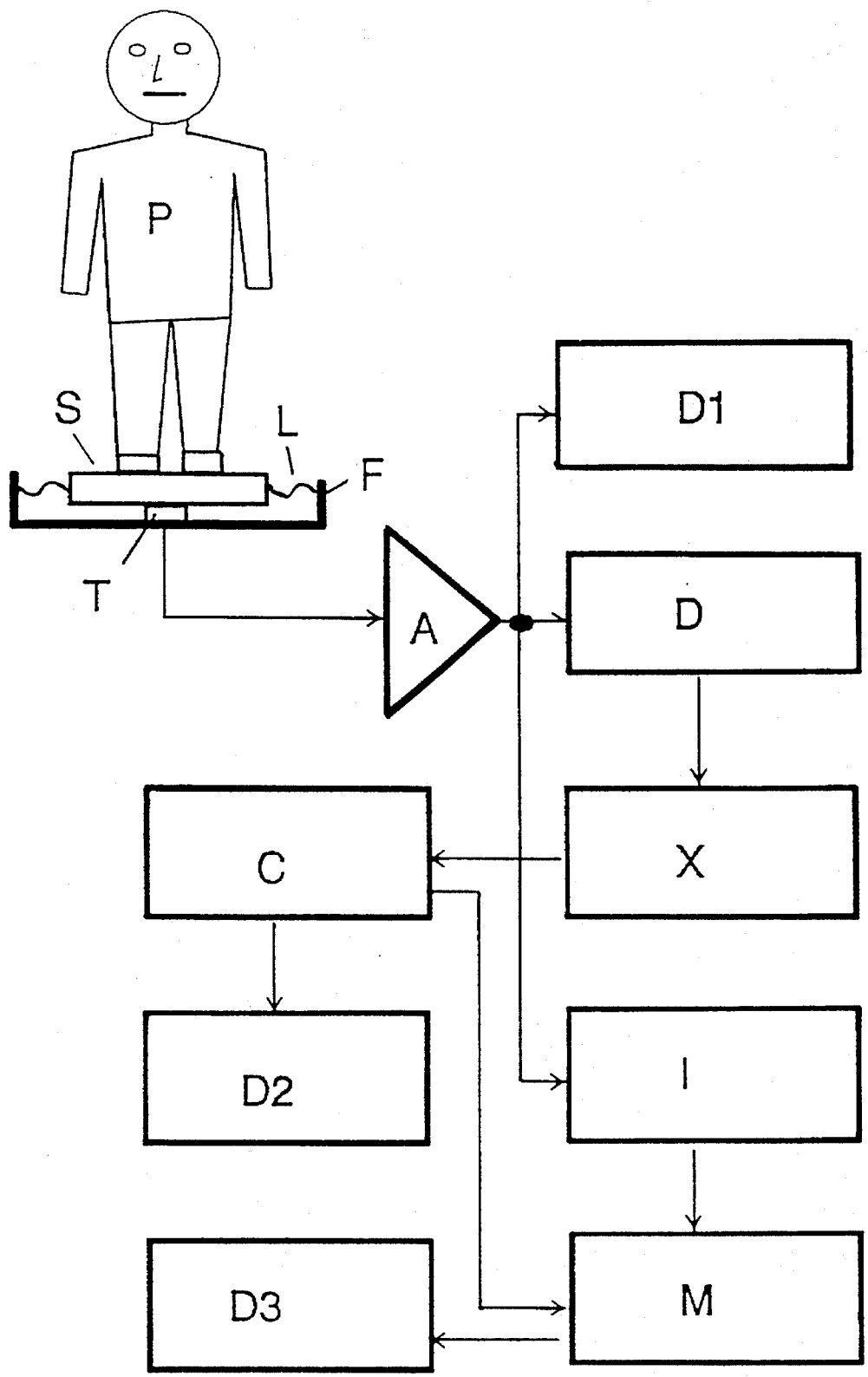
Figure 3A:
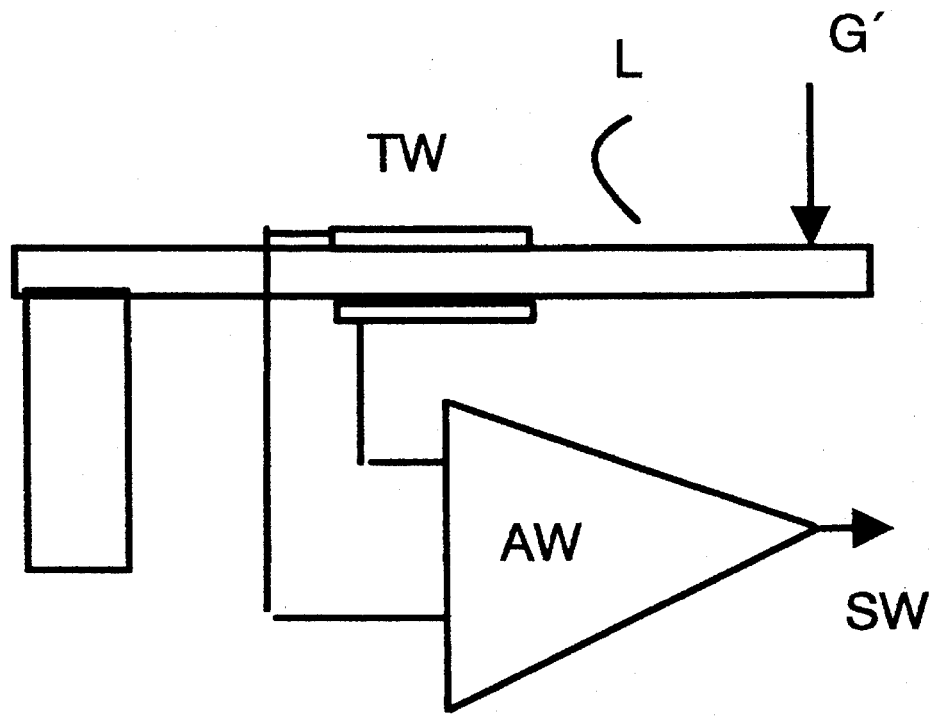
Figure 3B:
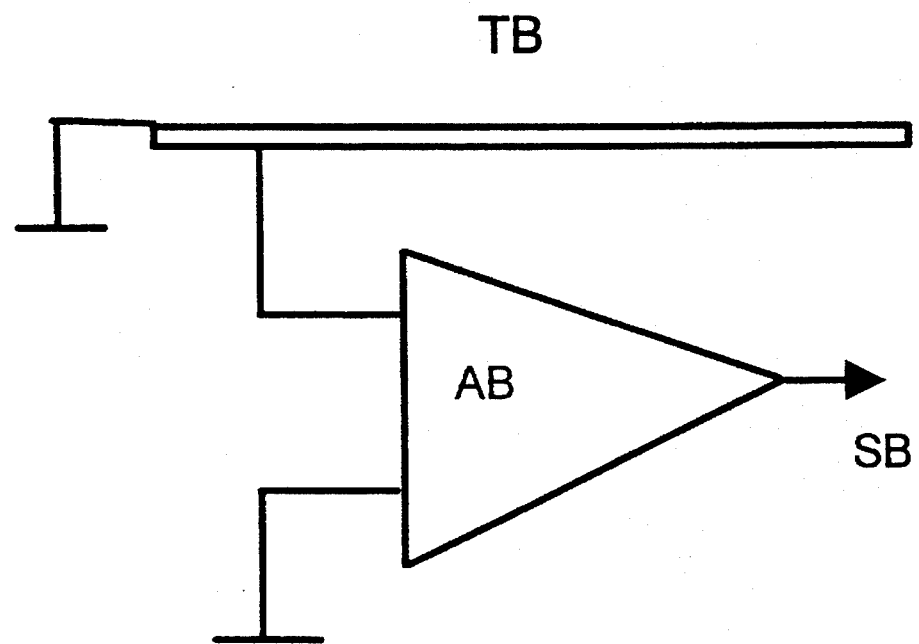
Figure 4:
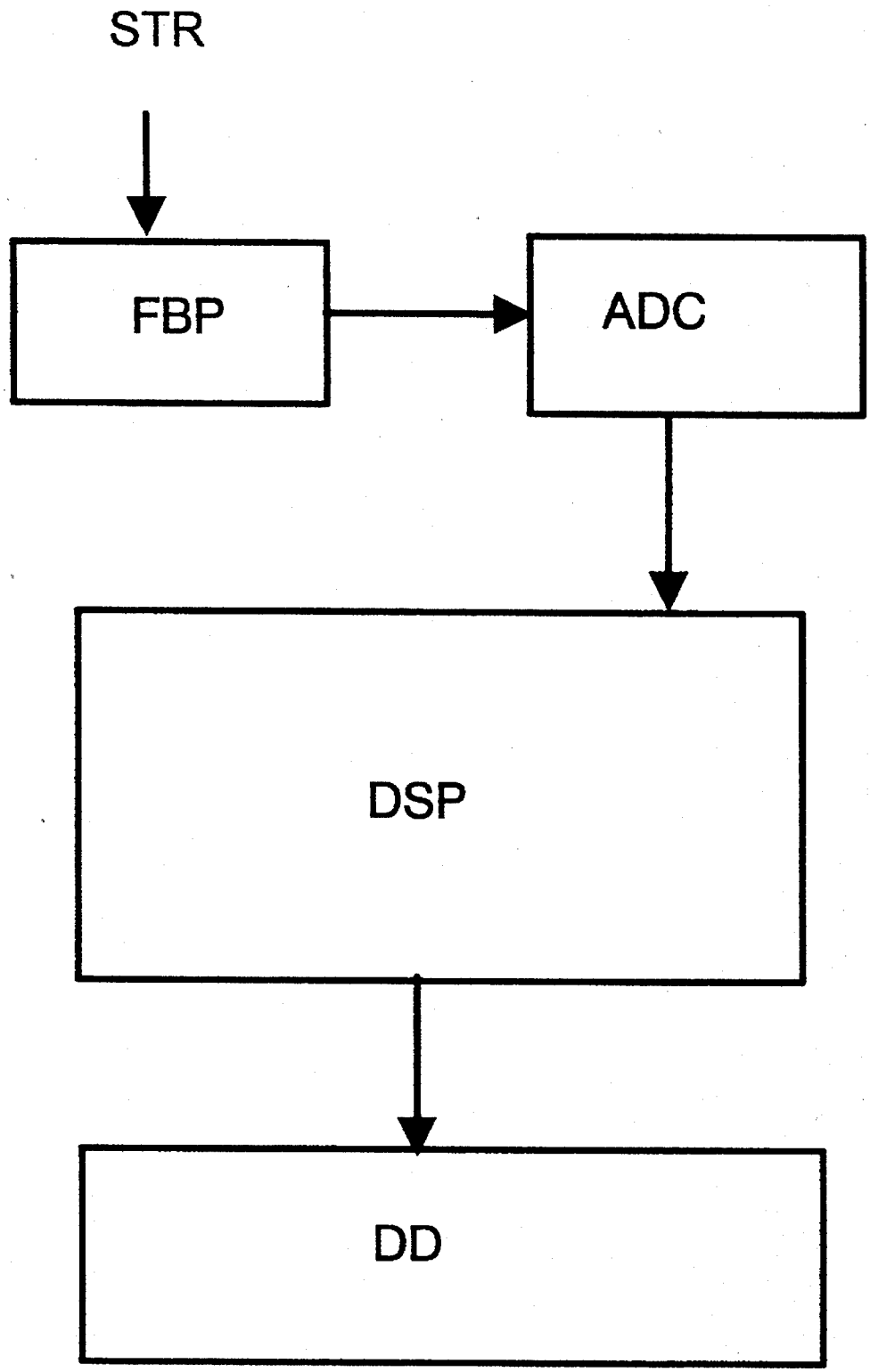
Figure 5A:
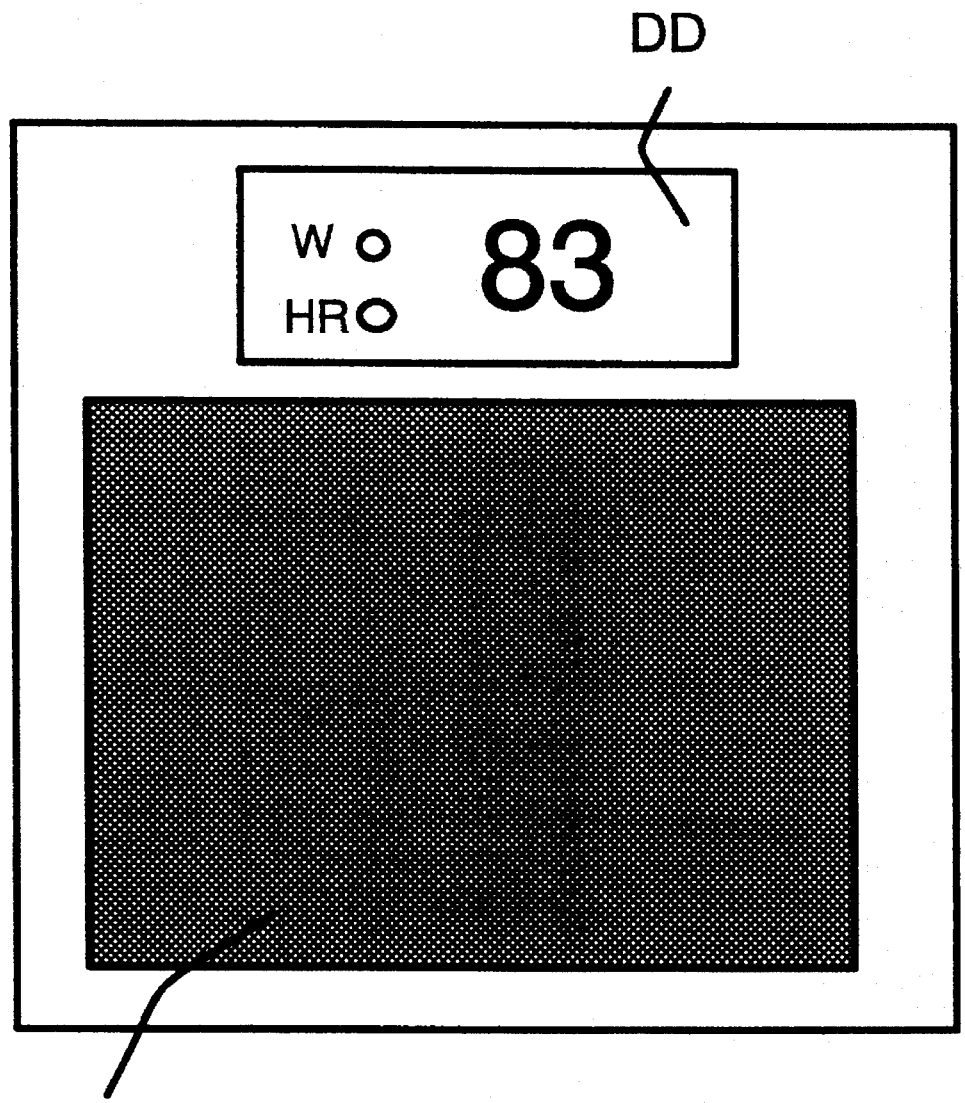
Figure 5B:
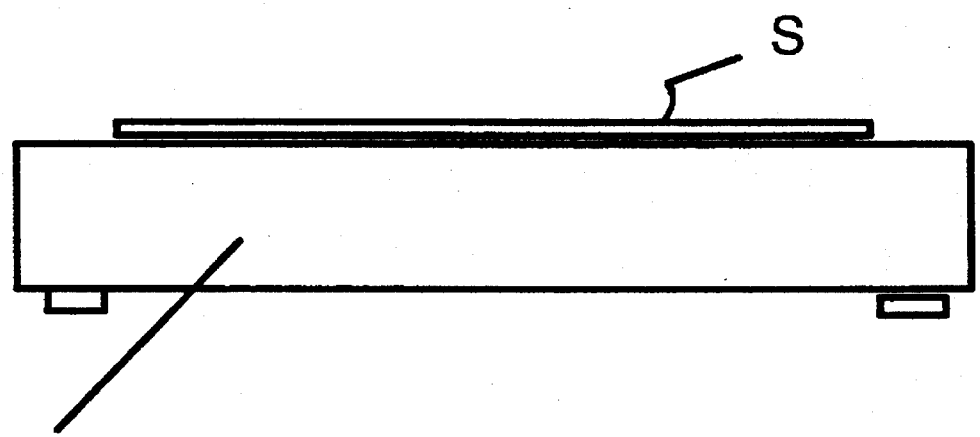

FIGS. 1A–1C are schematic views of forces developing in the circulatory system as a result of cardiac activity, FIG. 2 shows a block diagram for an apparatus of the invention, FIGS. 3A and 3B show two different transducer designs, FIG. 4 shows a block diagram for digital signal processing electronics in an apparatus of the invention, FIGS. 5A and 5B show one apparatus of the invention in a top and a side view, respectively.

FIG. 1A illustrates schematically those parts of a human circulatory system that are essential in view of understanding the working of the invention. The left ventricle of the heart H of a person P pumps on each stroke a pulse of bloodflow into the aorta AO, which results in a change of blood flow BF. The bloodstream turns in the aorta curve AC, which in turn produces a force FO directed towards the head of P as shown in FIG. 1B. FIG. 1C is a graphic representation of the changes of BF and the corresponding variations of weight G as a function of time t.

FIG. 2 illustrates an apparatus of the invention, wherein a person P stands on a measuring support S, which is suspended on a frame F by means of sensing elements L, e.g. springs. Support S is fitted with a transforming element T, e.g. a strain gage transducer or a piezo-electric crystal or ceramics for recording the movements of S which depend on the weight of P and the compliance of L. It should be noted that a similar signal is obtained if a person is set in a sitting position on S which is provided for example with a chair-like stand. A sitting position is feasible e.g. for poorly fit or handicapped persons or if long-term recording is desired. The output signal of T is amplified by means of an amplifier A, whose output is thus dependent on the weight of P and can be shown on a display D1. The output signal of A is carried to a derivator D, from whose output signal a pulse shaper X produces a pulse which corresponds to each fast weight change of P and which is forwarded to a central processor C, whose output provides HR shown on a display D2. X may also be provided with a detected-pulse indicator, a sound signal or a light signal or both. Another conceivable arrangement is such that the operator can select the type and intensity of an indicator signal at will or Switch it off completely. Integration of the change of the output signal of A with an integrator I provides a result proportional to stroke volume SV and multiplication of this with HR by a multiplier M provides a result proportional to cardiac output CO, which is shown on a display D3.

Transducer T may comprise several separate transducers. Several transducers may be used e.g. for reducing the fluctuation caused by the swaying of a standing person. An apparatus intended for the examination of a sitting person may include a chair-like measuring support and therebelow four weight transducers, whose signals are added together.

Furthermore, it may be beneficial to use a plurality of transducers such that a first transducer primarily records the weight of a person and a second transducer records variations of the weight of a person. This type of transducer circuit is chematically illustrated in FIG. 3. In the case of FIG. 3a, a force G' proportional to the weight of a patient applies to a sensing element L which is fitted with a transforming element Tw, possibly e.g. a strain gage transducer. Typically, this type of transducer includes two elements, whose resistance changes in the opposite directions as sensing element L flexes as a result of force G'. These transducer elements are connected to an amplifier Aw, whose output signal Sw is proportional to force G'. The current bathroom scales employ a circuit, wherein the frequency of an oscillator is altered under the control of a transforming element Tw and this frequency is used for the derivation of weight. This type of solution, both electrical and mechanical, is included e.g. in the Hanson Hi-Tech (Bathroom scale, model 881) scale, manufactured by Hanson Industries Limited, Ireland. If such a circuit is to be maintained, it is preferable to employ another transducer solution for recording the variations of weight. Such other transducer solution is schematically shown in FIG. 3b. A transducer Tb is positioned e.g. on a measuring support S, such it will be subjected to the direct or indirect action of a person's weight G. One preferred embodiment for transducer Tb involves the use of piezoelectric materials. Piezoelectric ceramic components are manufactured e.g. by N. V. Philips Gloeilampenfabrieken, Eindhoven, Holland. Applications of these have been described e.g. in the publication Piezoelectric Ceramic, Designer's Guide, Philips Component Division 1989. Transducer Tb is preferably designed e.g. by using a component consisting of two piezoelectric ceramic elements (piezoelectric bimorph). An advantage offered by such element is a relatively low electrical and mechanical impedance, which makes it particularly suitable for recording relatively low-frequency variables. The described-type of piezoelectric transducer can be included, as shown in FIG. 3a, in a flexible sensing element L and the obtained signal is forwarded to an amplifier Ab, whose output signal Sb is delivered to signal processing electronics. Another way of using a piezoelectric material is to provide support S with a layer of piezoelectric material, such as PVDF-film manufactured e.g. by Pennwalt Corp., PA, U.S.A and marketed on the tradename Kynar Piezo Film.

FIG. 2 shows just one block diagram for an apparatus of the invention. For example, a quantity proportional to CO is obtained more accurately by averaging the values of SV and HR. Thus, the apparatus must be provided with appropriate means for this purpose. In order to calculate an index representing physical condition or fitness, the above results can be converted e.g. into a digital form and a desired index can be calculated therefrom by means of a microprocessor. Thus, the apparatus must be provided with appropriate means for this purpose. The required A/D converters are manufactured e.g. by Motorola Inc. and Linear Technology Corp., U.S.A. and suitable microprocessors by Intel Corp., U.S.A. The obtained result or results may be stored in a memory and used later as a reference in assessing the progress of a person's fitness. The recording means may comprise e.g. a semiconductor memory or a magnetic, optical or magneto-optical disc, a magnetic tape or a so-called smart card or even a punched card or tape. A suitable microprocessor assembly, which is compatible with so-called IBM PC equipment, is manufactured e.g. by Dover Electronics Manufacturing West, U.S.A. The apparatus is of type ESP8680 and the necessary interface equipment is available therefor. In mass production, it is of course necessary to design a solution for the apparatus, which is economical in terms of production.

Instead of the embodiment shown in FIG. 2, the invention can be implemented by utilizing the spectral information included in a signal coming from the transducer. After transducer T and amplifier A, the signal is converted to a digital form and it is transformed in to frequency domain for example by using FFT algorith or so-called autoregressive algorithms (Autoregreesive algorithms and other analyzing methods, which are applicable when the number of samples picked up from the signal is small, have been described e.g. in the reference: Kay et al: Proceedings of IEEE, vol. 69, No. 11, 1981). This can be handily carried out in said PC equipment but dedicated signal processing circuits are also available. The resulting spectrum includes an intense peak correlating to the heart rate (i.e. HR) and multiples thereof. A simple program searches a suitable HR range for a maximum, which is HR at a given time. A suitable spectral range is 0.5–4 Hz, which corresponds to heart rates of 30–240 strokes/minute. This method is quick and not easily disturbed by the movements of a person. The periodicity of a signal can also be analyzed by using a correlation function. This type of solutions have been used in the analysis of periodical signals.

The aspects associated with spectral calculation and signal processing have been studied in a number of publications, including for example Proakis J. G. and Manolakis D. G.: Introduction to digital signal processing, Macmillan Publishing Company, New York, 1988 as well as Oppenheim A. V. and Schafer R. W.: Discrete-Time Signal Processing, Prentice-Hall International Inc., Englewood Cliffs, N.J., 1989.

Several prior known solutions can be applied in the apparatus, whose main principles have been described for example in the publication Tompkins W. J. and Webster J. G.: Design of microcomputer-based medical instrumentation, Prentice-Hall Inc., Englewood Cliffs, N.J., 1981. FIG. 4 illustrates a block diagram for an apparatus wherein a signal STR, coming from a transducer and, if necessary, amplified in a preamplifier, is forwarded to a filter FBP, from there to an A/D converter ADC and then to a processor DSP, whose output is advanced to a display DD. Filter FBP is a band pass filter which, when analyzing cardiac activity, eliminates the frequencies which do not include significant information or which include disturbing signals produced e.g. by the swaying of a person. The conducted tests have indicated that preferred frequency range is 6–15 Hz if the purpose is to record HR. It is preferred that the filter eliminates as effectively as possible low frequency (<1 Hz) components. The filter may be designed using the components and concepts of analog electronics or at least some of the filtering may be effected digitally by means of processor DSP.

A number of prior known principles may be applied in transducer solutions. Since the quantity to be measured is a person's weight G, which is essentially a force produced by a person's mass and the acceleration of earth gravity, the changes of weight caused by cardiac activity can be measured in a number of ways. The above description has primarily related to piezoelectric and piezoresistive transducer elements. It is prior known to measure variations of force by means of sensing elements, such that transformations (number of transformations, rate of transformations) of sensing elements are measured by using capacitive, inductive, optical and acoustic methods. These principles are described e.g. in publications: Allocca J. A. and Stuart A.:

Transducers: Theory and Application, Reston Publishing Company, Inc., Reston, 1984 as well as Cobbold R. S. C.: Transducers for Biomedical Measurements, John Wiley & Sons, New York, 1974. Combinations of prior known transducer principles may be used for implementing apparatus of the invention in a variety of ways. The selection of transducer principles depends on several factors, such as manufacturing costs, accuracy requirements and power consumption. In the simplest, so-called bathroom equipment, it is quite likely that the most preferred transducers are piezoresistive or piezoelectric. When recording changes of weight, a piezoelectric transducer produces a powerful signal which, on the other hand, depends e.g. on the ambient temperature. However, the solution may be preferable if the purpose is to record HR.

The results and calculated indices or a summary of results and calculated indices can be printed on paper numerically and also graphically in the form of curves for thus supplying a person with a detailed representation of his or her progress. The apparatus can also be provided with signaling means, light or sound, which informs of the detection of heartbeat. As mentioned above, these means may be coupled to the pulse shaper. The apparatus may be fitted with or it may be connected to a necessary printing means, for example a matrix or laser printer. Suitable printers are manufactured for example by Canon Inc., Japan.

For example, the monitoring of physical fitness can be effected e.g. by using indices R calculated as follows:

$R = c/(HR*G)$, or $R = 1/(HR*G)$, wherein c is a number proportional to a person's SV or CO and derived from the measuring results. It is preferred that the values used for SV and CO as well as HR are averages obtained during a period of several heartbeats. As a long term result of physical conditioning, the rest-measured HR of the heart decreases and SV increases quite rapidly but the changes of weight generally occur slowly. As a person's physical condition improves, R calculated as above rises rapidly, this being a more responsive indicator of the direction of progress than mere body weight. Thus, R can be used as a support for weight-losing diets and fitness programs. An index indicating rapidly improving fitness improves considerably motivation for training and dieting.

The above describes just one simple way of using measured quantities for calculating an index indicating the progress or status of condition. The index formula may be adapted to include e.g. a target weight, whereby the index progress and approach towards the target are clearly discernible. Also, different quantities may be given different emphases depending on the target of a training or weight-losing program.

Depending on the versatility of signal processing, the calculated indices may be personal reference numbers, whereby the indices of different persons cannot be directly compared. If the signal processing is sufficiently versatile and the positioning of a person is handled carefully, it is possible to derive indices and measuring results that may be used for the relative comparison of different persons. The positioning can be assisted by using e.g. a chair-like measuring support, whose back rest is tiltable for thus finding the maximal change of weight caused by cardiac activity. The reason for this is that the direction of aorta curve relative to the body is different in different persons.

The invention may be applied e.g. in domestic (bathroom) scales. In its simplest form, such a scale would display the weight and HR of a person. For such a scale, it is possible to develop a custom-specific integrated circuit. Separate displays are not required but HR and weight may automatically alternate on the display or the display may be selected e.g. with a separate switch, remote control or a the like. One such an apparatus is depicted on FIG. 5. FIG. 5a illustrates the top view of the apparatus. FIG. 5b is a side view of the apparatus. The measuring support S is in the frame F. The realization of the transducer means affects on the construction of the apparatus. Mechanically the construction of the apparatus may be similar than the construction of the above mentioned Hanson scale if e.g. strain gage transducer is utilized. In the display means DD there are indicators for HR and W display modes. In the HR mode the HR indicator is lighted up and the display shows HR e.g. in beats per minute. Correspondingly, in the W mode the display shows the weight of the person in kg:s or lbs and the W indicator is lighted up. The indicators may be e.g. light emitting diodes (LED:s) or specific signs in a liquid crystal display. One benefit of the alternating display described above is the reduction of manufacturing costs. The alternating display saves also space and the figures in the display may be designed to be of large size.

The display may also be fitted on a stand or be mechanically separated from F. The communication between the display unit and the electronics near or in F may take place via wires, infrared light, (ultra)sound, capacitive or inductive coupling or radio waves. A benefit of this kind of remote display is that the person does not need to bow as he or she reads the display. The bowing movement changes the posture of the thorax and affects on the values of the possibly measured quantities related to SV and CO.

The more elaborated devices of the invention calculate fitness indices for a person and may display quantities proportional to CO and SV. Such devices are useful for exercisers, athletes and may be available in private homes, health spas, gyms etc. Devices intended for public use may be provided with a coin mechanism or a card reader for controlling the use.

In more demanding use, more attention must be paid to the positioning of a person being examined and a good solution is a chair-like measuring support, having more than one transducers (for example 3 or 4) therebelow. The support may be provided with a tiltable back rest as well braces for setting a person repeatedly in the same position. The back rest and other braces must be provided with scales or the like, whose readings are marked down or recorded in the memory of such apparatus for future measurements. Such braces may be motorized and the motors may be controlled by the computer of the apparatus to measuring positions e.g. on the basis of a personal identification code. Naturally, a method of the invention and corresponding devices may be used in many types of psycho-physical tests, in monitoring the treatment of illnesses etc.

Monitoring SV and CO has been found beneficial when observing the treatment of atrial fibrillation and the effect of a by-pass operation. Likewise, it is conceivable to use the changes of SV and CO for assessing the treatment of cardiac insufficiency. A method of the invention and devices based thereon are capable performing this easily and economically.

The above only describes a few embodiments of the invention. The invention can be subjected to a plurality of modifications within the scope of the inventive concept defined in appended claims.

I claim:

1. A method for measuring quantities relating to a person's physical condition and cardiac activity, such as a person's weight and quantities proportional to heart rate, cardiac stroke volume, and cardiac output, characterized by:

positioning a person on a measuring support so that a blood flow pulse caused by a stroke of the heart is matched by a change in the weight;

recording the person's weight and changes in the weight;

using time related characteristics of the recorded changes in the weight to determine information about the person's cardiac activity including at least one of the quantities proportional to heart rate, cardiac stroke volume, and cardiac output; and, deriving said quantity related to the person's physical condition from said weight and said at least one of the quantities proportional to heart rate, cardiac stroke volume, and cardiac output.

2. A method as set forth in claim 1, further characterized by; using amplitude related characteristics of the recorded changes for deriving said information about said quantities related to the person's physical condition and cardiac activity.

3. A method as set forth in claim 1 further characterized by: calculating a frequency spectrum for the changes of weight.

4. A method as set forth in claim 1 further characterized by: calculating a correlation function for the changes of weight.

5. A method as set forth in claim 1 further characterized by: calculating the quantities proportional to heart rate, stroke volume and cardiac output by using quantities proportional to the time integral of the changes of weight.

6. A method as set forth in claim 5 further characterized in that the quantities are utilized for calculating an index representing the physical condition of a person that includes a correlation to the weight.

7. A method as set forth in claim 6, characterized in that said index representing a person's physical condition includes a correlation to one of the heart rate and the cardiac stroke volume.

8. An apparatus for measuring variables relating to a person's physical condition and cardiac activity, such as a person's weight and quantities proportional to the weight, heart rate, cardiac stroke volume, and cardiac output, characterized by:

a measuring support for positioning a person thereon, so that a blood flow pulse caused by a stroke of the heart is matched by a change in the weight;

a recording device for recording the person's weight and changes in the weight;

means for deriving the quantities related to the person's cardiac activity by utilizing time related characteristics of the recorded changes in the weight; and, means for deriving said quantity related to the person's physical condition from said weight and said quantities related to the person's cardiac activity.

9. An apparatus as set forth in claim 8, characterized in that it includes means for deriving said quantities related to the person's cardiac activity and physical condition by utilizing amplitude related characteristics of the recorded changes of weight.

10. An apparatus as set forth in claim 9 further characterized by a transducer that produces one of electrical impedance changes and a voltage depending on the weight and its changes.

11. An apparatus as set forth in claim 10 further characterized by an amplifier and filter for using the output signal of the transducer to derive therefrom a signal proportional to the changes of weight relating to the person's cardiac activity.

12. An apparatus as set forth in claim 11 further characterized by: means for calculating quantities proportional to a time integral of the changes of weight.

13. An apparatus as set forth in claim 12 further characterized by: means for calculating a frequency spectrum for the changes of weight.

14. An apparatus as set forth in claim 12 further characterized by means for calculating an index representing the person's physical condition.

15. An apparatus as set forth in claim 8 further characterized by means for recording and displaying measured and calculated results and calculated condition-represented indices.

16. An apparatus as set forth in claim 15 further characterized in that it includes means for controlling use of the apparatus.

17. An apparatus as set forth in claim 15 further characterized in that it includes a sensory indicator that indicates the detection of a change of weight.

18. An apparatus as set forth in claim 8 characterized in that said measuring support is provided with a plurality of transducers.

19. An apparatus as set forth in claim 18 further characterized in that some of the transducers record the weight and some of the transducers record the changes of weight.

20. An apparatus as set forth in claim 8 further characterized in that it includes a positioning mechanism for providing standard and repeatable upright positions of the person's body on said measuring support.

* * * * *